United States Patent
Kibler et al.

(10) Patent No.: US 11,806,538 B2
(45) Date of Patent: Nov. 7, 2023

(54) METHOD FOR PROGRAMMING AN IMPLANTABLE MEDICAL DEVICE AND SYSTEM FOR CONFIGURING STIMULATION PARAMETERS OF AN IMPLANTABLE MEDICAL DEVICE

(71) Applicant: BIOTRONIK SE & CO. KG, Berlin (DE)

(72) Inventors: Andrew B. Kibler, Lake Oswego, OR (US); Lauren Kraiter, Tigard, OR (US); Larry Stotts, Tigard, OR (US)

(73) Assignee: BIOTRONIK SE & Co. KG, Berlin (DE)

( * ) Notice: Subject to any disclaimer, the term of this patent is extended or adjusted under 35 U.S.C. 154(b) by 0 days.

(21) Appl. No.: 17/747,011

(22) Filed: May 18, 2022

(65) Prior Publication Data
US 2022/0273957 A1 Sep. 1, 2022

Related U.S. Application Data

(63) Continuation of application No. 16/825,665, filed on Mar. 20, 2020, now Pat. No. 11,357,990.
(Continued)

(51) Int. Cl.
*A61N 1/02* (2006.01)
*A61N 1/05* (2006.01)
(Continued)

(52) U.S. Cl.
CPC ......... *A61N 1/37241* (2013.01); *A61N 1/025* (2013.01); *A61N 1/3605* (2013.01); *A61N 1/0551* (2013.01)

(58) Field of Classification Search
CPC .. A61N 1/37241; A61N 1/025; A61N 1/3605; A61N 1/0551; A61N 1/36139; A61N 1/36142; A61N 1/36171; A61N 1/36175; A61N 1/37247; A61N 1/36062; A61N 1/0558; A61N 1/36135; A61N 1/0529; A61N 1/0531; A61N 1/0534; A61N 1/0536; A61N 1/0556; A61N 1/36002;
(Continued)

(56) References Cited

U.S. PATENT DOCUMENTS

| | | | |
|---|---|---|---|
| 11,357,990 B2 * | 6/2022 | Kibler | A61N 1/36062 |
| 2015/0012063 A1 * | 1/2015 | Chen | A61N 1/37235 |
| | | | 607/59 |

(Continued)

*Primary Examiner* — Carl H Layno
*Assistant Examiner* — Anh-Khoa N Dinh
(74) *Attorney, Agent, or Firm* — Laurence A. Greenberg; Werner H. Stemer; Ralph E. Locher (57) ABSTRACT

A method programs an implantable medical device to configure the implantable medical device for stimulating neural tissue by at least one electrode. The method includes: performing, by the implantable medical device, an evoked compound action potential (eCAP) threshold search by stimulating the neural tissue with test stimulation pulses; determining, based on the eCAP threshold search, an eCAP threshold amplitude and a coupling factor that is indicative of a coupling between the at least one electrode and the neural tissue; and generating a first set of stimulation parameters containing at least a stimulation amplitude that is determined in dependence on the eCAP threshold amplitude and the coupling factor.

17 Claims, 6 Drawing Sheets

Related U.S. Application Data (60) Provisional application No. 62/829,661, filed on Apr. 5, 2019.

(51) Int. Cl.
*A61N 1/36* (2006.01)
*A61N 1/372* (2006.01)

(58) Field of Classification Search
CPC ............ A61N 1/36053; A61N 1/36071; A61N 1/36182; A61N 1/37205; A61N 1/37518; A61N 1/406; A61N 7/00
See application file for complete search history.

(56) References Cited

U.S. PATENT DOCUMENTS

| | | | |
|---|---|---|---|
| 2015/0012064 A1* | 1/2015 | Chen | A61N 1/05 607/59 |
| 2017/0120062 A1 | 5/2017 | Kumar | |
| 2018/0126169 A1 | 5/2018 | Hou et al. | |

* cited by examiner

METHOD FOR PROGRAMMING AN IMPLANTABLE MEDICAL DEVICE AND SYSTEM FOR CONFIGURING STIMULATION PARAMETERS OF AN IMPLANTABLE MEDICAL DEVICE

CROSS-REFERENCE TO RELATED APPLICATION

This application is a continuation of patent application Ser. No. 16/825,665 filed Mar. 20, 2020, now U.S. Pat. No. 11,357,990 B2, under 35 U.S.C. § 120; this application also claims the benefit, under 35 U.S.C. § 119(e), of provisional patent application No. 62/829,661 filed Apr. 5, 2019; the prior applications are herewith incorporated by reference in their entirety.

FIELD AND BACKGROUND OF THE INVENTION

The instant invention generally relates to a method for programming an implantable medical device. The current invention also relates to a system for configuring stimulation parameters of an implantable medical device.

Neuromodulation consists of the delivery of electrical, magnetic, mechanical, thermal, optical, or pharmaceutical stimuli to the central or peripheral nervous system of a patient. To this end, an implantable medical device may be implanted in the patient's body, wherein the implantable medical device is configured for stimulating neural tissue, e.g., by means of one or more electrodes. A common example of such an implant-based neuromodulation therapy is the spinal cord stimulation (SCS), in which case the implantable medical device comprises an implantable pulse generator (IPS) and typically two leads which extend along the spinal cord and have a plurality of electrodes (for example 8 electrodes per lead) that couple to the neural tissue at different locations along the spinal cord.

Generally, neuromodulation results in a perturbance of the tissue under stimulation in the form of (most commonly) transmembrane depolarization, action potentials, changes in extracellular ionic concentrations, or synaptic transmitter release. Such perturbations are adapted to deliver a therapeutic effect to a patient. A strength of the perturbations must be titrated (i.e., dosed) to elicit the desired effect at the required strength and with a minimum of side effects. A titration (i.e., dosage) process typically requires an adjustment of a strength, duration, frequency, and/or location of the stimulation. Often, certain combinations of these parameters may elicit undesired side effects including overstimulation, which may be uncomfortable for the patient or cause other more serious effects, such as bradycardia in the case of a vagus nerve stimulation (VNS).

The neuromodulation parameters of an implantable medical device need to be (re-)programmed from time to time. It is desirable to perform the (re-)programming and adjustment of the neuromodulation remotely, e.g., by means of an external programmer device which adjusts neuromodulation parameters of the patient's device while the patient is at their home. Travel requirements and use of other resources for the patient and/or a clinician may thus be decreased. Further, remote programming may permit rapid diagnostics and adjustment of the implant and an increased availability of assistance to patients in the management of their chronic condition.

One of the most common use cases that may be facilitated by remote programming in the SCS neuromodulation field is the adjustment of a patient's stimulation program in response to, e.g., changing pain area, lead migration, or neural habituation to the existing stimulation program. For example, U.S. patent publication No. 2017/0120062 A1 describes a remote programming workflow for SCS devices using a remote programmer.

A significant risk of remote programming is the temporary delivery of uncomfortable stimuli as the stimulation program parameters are changed. Additional risks include: an incorrect patient feedback and resulting incorrect setting of therapy parameters; a sudden change in stimulation contact proximity to a target tissue, leading to a sudden overstimulation; an incorrect operation of controls by the patient, leading to uncomfortable stimulation; a loss of remote connection to a patient device, leaving it in an unknown or undesired state; and a potential inability of a patient to stop an uncomfortable stimulation, leading to prolonged uncomfortable stimulation and potentially more serious side effects.

Some known solutions to address these risks put the patient in the feedback loop during remote parameter titration, e.g. by requiring the patient to press a button in order to adjust parameters, or to indicate when sensations are felt. In another approach, the patient may be asked to provide verbal feedback, although there is an intrinsic delay and lack of precision with this approach. In any case, such solutions rely on the patient being cognitively able to actively and accurately participate.

Further solutions attempt to minimize the patient's discomfort by monitoring adjunct physiological parameters, such as heart rate, blood pressure, muscle responses, or eye movements. However, such secondary physiological measures may vary greatly from patient to patient and may also require a significant episode of discomfort to occur before detection.

Another known solution is based on a remote device adjustment in which a limited set of pre-programmed and tested parameter combinations are sequentially selected, often by directing the patient to perform some selection action of these existing combinations over the phone.

In summary, the existing remote titration concepts described above have the below described drawbacks.

An inclusion of the patients in the remote programming loop, whether by asking them for feedback or asking them to operate their device in a way that may lead to uncomfortable stimulation, requires that the patients be completely aware of the control they possess, its potential ramifications, and the actions they should take in the event of uncomfortable stimulation. This limits the patient population applicable to this approach. The risk of uncomfortable stimulation remains.

Solutions which require the patient to feel and respond to stimulation suffer from the drawback that patient response and experience of stimulation is highly variable, and may induce significant bias in the titration results. For example, in an SCS scenario, a strong-willed patient may allow or induce an up-titration of their stimulation which is too high or borderline uncomfortable, because they feel that stronger stimulation may be more effective. Likewise, a patient may become confused about whether a sensation is related to their stimulation or to their condition, or if the sensation is just caused by the fact that they are being asked to sit still in one position for a period of time.

For solutions where a number of pre-set and tested programs are available for use in a remote programming setting, there is an intrinsic limitation as to the adjustments that can be made. This limitation is based on which programs have been conceived and programmed a priori. In addition, changes in a stimulation target or a tissue response may invalidate these preset programs or cause them to be unexpectedly uncomfortable or ineffective when activated.

For proposed solutions which require a secondary physiological factor response of the patient, the stimulation parameters must already be outside of the desired range, and perhaps uncomfortable, which is undesirable and should be avoided.

U.S. patent publication No. 2018/0126169 A1 describes an iterative method for determining SCS stimulation parameters using evoked compound action potentials (eCAPs) as feedback parameters. Methods of collecting eCAP signals for analysis are known in the art. Essentially, in such schemes, one or more stimulation pulses are provided to a target tissue via one or more stimulating electrodes. When the stimulation is supra-threshold to exciting the target neurons, an eCAP from the stimulated neurons may be recorded via adjacent electrodes. The evoked neural response lasts typically between 1 ms and 10 ms, depending on the distance between stimulating and recording electrodes, and neural properties. There is no detectable eCAP at subthreshold stimulation amplitudes.

SUMMARY OF THE INVENTION

It is an object of the present invention to provide an improved method for programming an implantable medical device. For example, it is desirable to provide for a safe remote programming of a patient's implanted neuromodulation unit in a way which does not induce uncomfortable sensations, does not limit the program parameters to a pre-determined set, and does not involve the patient by requiring feedback during a critical phase of testing. Further, there is a desire for providing a device system which supports such a method.

According to a first aspect of the current invention, a method for programming an implantable medical device that is configured for stimulating neural tissue by means of at least one electrode is presented. The method comprises at least the following steps: performing, by means of the implantable medical device, an evoked compound action potential (eCAP) threshold search by stimulating the neural tissue with test stimulation pulses; determining, based on the eCAP threshold search, an eCAP threshold amplitude and a coupling factor that is indicative of a coupling between the at least one electrode and the neural tissue; and generating a first set of stimulation parameters comprising at least a stimulation amplitude that is determined in dependence on the eCAP threshold amplitude and the coupling factor.

Hence, it is proposed to determine, by means of an eCAP threshold search, a coupling factor (such as an electrode-spinal cord coupling factor in the case of SCS) in addition to an eCAP threshold amplitude. The coupling factor is indicative of a present coupling between the at least one electrode (or several electrodes, depending on the configuration) and the neural tissue. In particular, the coupling factor may take into account stimulation pulse parameters which induced the eCAP, recent changes of a pain area, lead migration, or neural habituation.

In accordance with an embodiment, the coupling factor may be determined in dependence on the eCAP threshold amplitude and a ratio of a change in eCAP amplitude to a corresponding change in a stimulation amplitude. For example, the changes may be measured directly above the eCAP threshold amplitude. In other words, the coupling factor may be calculated at least partially based on a slope of a curve indicating the eCAP amplitude in dependence on the stimulation amplitude as measured slightly above the eCAP threshold (e.g. between a value of the stimulation amplitude corresponding the threshold and 10-20% above the value).

For example, the coupling factor may be determined such that the lower the eCAP threshold amplitude the higher the coupling factor, and the higher the ratio the greater the coupling factor. Based on preclinical research results, a coupling factor determined in this way may be a good indication of the coupling of the stimulation electrodes to the neural tissue.

For example, the eCAP threshold search may comprise delivering stimulation with consecutive test stimulation pulses having an increasing amplitude until an eCAP is detected for at least two consecutive amplitudes. The eCAP threshold amplitude may then be determined, for example, by means of a linear regression fit.

For another example, the eCAP threshold search may comprise delivering stimulation with consecutive test stimulation pulses having an increasing pulse width until an eCAP is detected for at least two consecutive widths. The eCAP threshold width may then be determined, for example, by means of a linear regression fit.

According to an embodiment, the test stimulation pulses used for the threshold search are shorter than 300 μs. Additionally or alternatively, it may be provided that the test stimulation pulses are delivered with a stimulation frequency in the range from 40 Hz to 60 Hz. A comfortable patient experience may thus be achieved. The applicant has engaged in a significant clinical SCS study which investigated the impact of stimulation frequency, pulse width, and electrode selection on patient perception and comfort level of stimulation. Contrary to recent previous studies which used implantable stimulators to provide test stimulation, highly precise benchtop equipment was employed to deliver controlled stimuli with validated output across all stimulation combinations. Study results indicate that a stimulation-induced paresthesia comfort is maximized at frequencies below 2 kHz, preferably 40-60 Hz, and that on average the limit of comfortable stimulation is 10-15% above the perception threshold of stimulation, indicating a target operating window in which to perform eCAP measurements.

According to a variant embodiment, the method is carried out iteratively in such a way that, in an iteration step, the eCAP threshold step is performed in dependence on the first set of stimulation parameters as generated in a preceding iteration step. The accuracy of the parameter adjustment may thus be increased and the time to measure the threshold and coupling factor decreased.

Further, in an embodiment, the method comprises stimulating, by means of the implantable medical device, the neural tissue according to the first set of stimulation parameters. The knowledge of the coupling factor may thus be leveraged during the remote programming session, such that optimal therapy levels for the patient may be applied.

According to an embodiment, the method further comprises, before performing the eCAP threshold search: sending, via a remote data connection, a second set of stimulation parameters from a programmer device to the implantable medical device, wherein the eCAP threshold search is performed in dependence on the second set of stimulation parameters.

In a first variant of the above embodiment, the method further comprises, before sending the second set of stimulation parameters: selecting, by means of the programmer device, a set of intended stimulation parameters; and determining, by means of the programmer device and in dependence on the set of intended stimulation parameters, the second set of stimulation parameters as a set of test stimulation parameters suitable for the eCAP threshold search. In other words, a clinician may, for example, select a set of stimulation parameters that are a priori intended for therapy based on a clinical analysis of the patient's condition. This set of intended stimulation parameters may then be translated into a set of test stimulation parameters that are suitable for the eCAP threshold search before being sent to the IMD 1 as the second set of stimulation parameters.

In a second variant of the above embodiment, the method further comprises, before performing the eCAP threshold search: determining, by means of the implanted medical device and in dependence on the second set of stimulation parameters, a set of test stimulation parameters suitable for the eCAP threshold search, wherein the eCAP threshold search is performed in dependence on the set of test stimulation parameters. In this variant, which is alternative to the first variant, the second set of stimulation parameters may, for example, correspond to a set of intended stimulation parameters selected by a clinician. In contrast to the first variant, a translation into a set of test stimulation parameters suitable for the eCAP threshold search may be carried out at the end of the implantable medical device and patient remote control.

In accordance with the above embodiment, in both the first and the second variant, the set of test stimulation parameters may be determined, for example, by translating a stimulation pulse width and/or a stimulation frequency of a set of intended stimulation parameters (e.g., in the second variant in the form of the second set of stimulation parameters) into another stimulation pulse width and/or stimulation frequency. For example, the translation may be based on one or more a strength-duration curves and/or on one or more strength-frequency curves that may be stored in a memory of the implantable medical device and/or in a memory of a subject remote and/or in a memory of the programmer device.

In a further development of the above embodiment, the method further comprises: sending, via the remote data connection, a result of the eCAP threshold search from the implantable medical device to the programmer device; generating, by means of the programmer device, the first set of stimulation parameters based on the result; and sending, via the remote data connection, the first set of stimulation parameters from the programmer device to the implantable medical device.

It should be noted that the generation of the first set of stimulation parameters may optionally involve a user input (e.g. by a clinician) at the programmer device. Alternatively, the generation of the first set of stimulation parameters may be effected automatically by the programmer device.

According to a second aspect of the instant invention, a system for configuring stimulation parameters of an implantable medical device comprises: an implantable medical device that is configured for stimulating neural tissue by means of at least one electrode; and a programmer device having a remote (e.g., at least partially wireless) data connection with the implantable medical device; the implantable device being configured for performing an eCAP threshold search by stimulating the neural tissue with test stimulation pulses and for transmitting a result of the eCAP search to the programmer device via the remote data connection; the programmer device being configured for supporting a generation of a first set of stimulation parameters in dependence on the result of the eCAP threshold search and for transmitting the first set of stimulation parameters to the implantable medical device via the remote data connection; wherein the results of the eCAP search comprise an eCAP threshold amplitude and a coupling factor that is indicative of a coupling between the at least one electrode and the neural tissue; and/or the programmer device is configured for determining, based on the results of the eCAP search, an eCAP threshold amplitude and a coupling factor that is indicative of a coupling between the at least one electrode and the neural tissue.

For example, the programmer device is configured for supporting the generation of a first set of stimulation parameters in dependence on the eCAP threshold amplitude and the coupling factor.

Also in the present context, it should be noted that the generation first set of stimulation parameters may optionally involve a user input (e.g. by a clinician) at the programmer device. Alternatively, the generation of the first set of stimulation parameters may be effected automatically by the programmer device.

The system according to the second aspect of the present invention may be used for carrying out the method of the first aspect of the present invention. In other words, the components of the system according to the second aspect may be configured for carrying out corresponding method steps. For example, the implantable medical device of the second aspect may correspond to the implantable medical device referred to in connection with the method according to the first aspect. Likewise, the programmer device of the system according to the second aspect may correspond to the programmer device referred to in connection with the method according to the first aspect. Correspondingly, what has been described above and will be described in the following with reference to the method of the first aspect, may analogously apply to the system according to the second aspect, and vice versa.

In an embodiment of the second aspect of the present invention, the implantable medical device and/or the patient remote and/or the programmer device comprises a processor and a memory, the memory having stored thereon a computer program that causes the processor to execute some or all method steps according to the first aspect of the invention. This is to say that the respective processor (i.e., a processor of implanted medical device or a processor of the programmer device) may execute respective method steps that may be carried out by the implanted medical device or the programmer device, respectively.

In an embodiment, the method according to the first aspect of the present invention may be performed using the system according to the second aspect of the present invention by carrying out one or more of the following steps:

Prior to remote programming the implantable medical device, it may be established for a particular patient, e.g., in a clinic, that eCAPs may be recorded at certain comfortable stimulation levels.

A clinician chooses desired new therapy parameters (possibly including selected electrodes) as an intended set of stimulation parameters for the patient.

In a preferred variant, the system, either automatically or with input from the clinical user, translates the therapy parameters to comfortable parameters for an eCAP threshold search (a set of test stimulation parameters).

The system sends one or more commands to the implantable medical device to execute the eCAP threshold search with the set of test stimulation parameters.

The system stores, at least temporarily, the results of the eCAP threshold search.

The system analyzes the results of the eCAP threshold search to determine a coupling factor indicative of an electrode/tissue coupling specific to the patient and the employed leads/electrodes.

The system applies the coupling factor (and a pulse width translation if the preferred variant was taken above) to the set of intended stimulation parameters to determine a first set of stimulation parameters, which includes a therapy target amplitude and a maximum stimulation a parameter range to be used for the remote programming.

Upon confirmation by the clinician, the remote control unit sends the determined therapy program parameters and range (i.e., the first set of stimulation parameters) to the patient implant for therapeutic use on the patient.

In summary, the method according to the first aspect of the invention and the system according to the second aspect of the invention advantageously enable remote programming of an implantable medical device, whereby the patient will not experience uncomfortable sensations, and the process of parameter tuning will occur rapidly and automatically based on direct physiological feedback. The method and the system are applicable, for example, to both paresthesia and paresthesia-free SCS therapy styles, as well as other neuromodulation therapies.

Thus, the present invention enables a closed-loop based remote programming strategy that resolves many of the challenges related to safety, patient comfort, and accuracy that are intrinsic with the current state-of-the-art solutions. In particular, the proposed method may reduce a time needed to titrate a therapy, it may eliminate uncomfortable paresthesia during the remote programming, and it may provide a suitable patient-specific therapy amplitude in a safe manner. In addition, a therapy outcome may be improved by simplifying the patient management workflow Other features which are considered as characteristic for the invention are set forth in the appended claims.

Although the invention is illustrated and described herein as embodied in a method for programming an implantable medical device and a system for configuring stimulation parameters of an implantable medical device, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

In the following, embodiments of the invention shall be described in detail with reference to the drawings. In the drawings, like reference numerals designate like structural elements.

It is to be noted that the embodiments are not limiting for the invention, but merely represent illustrative examples.

Figure 1:
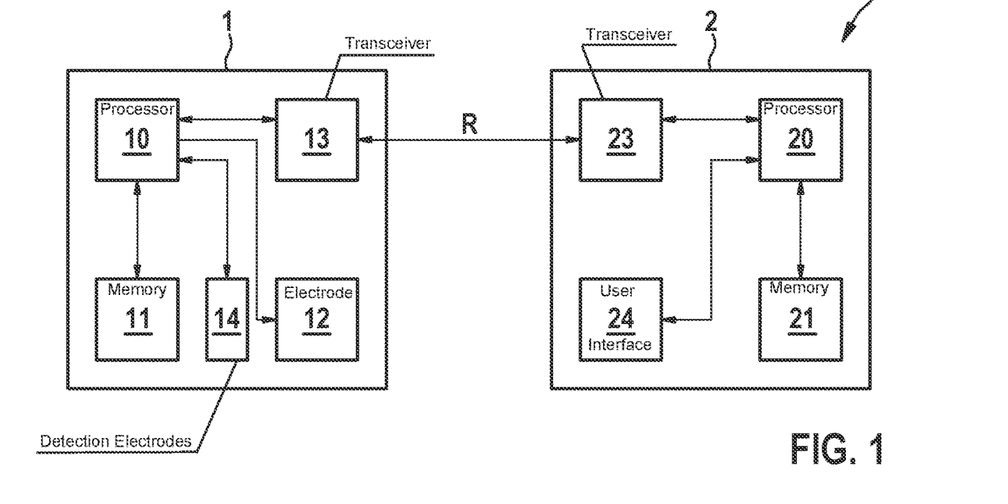
FIG. 1 is a block diagram showing a system comprising an implantable medical device and a programmer device in accordance with one or more embodiments and according to the invention.

Referring now to the figures of the drawings in detail and first, particularly to FIG. 1 thereof, there is shown a schematic and exemplary view of a system 3 comprising an implantable medical device 1 and a programmer device 2 in accordance with one or more embodiments.

The implantable medical device 1 (IMD) is configured for stimulating neural tissue by means of at least one electrode 12. For example, the IMD 1 may be configured for delivering an SCS therapy by means of leads extending along the spinal cord nervous system, each lead having a plurality of electrodes 12 arranged in contact with respective portions of the nervous tissue in the spinal cord. Further, the IMD 1 is equipped with one or more detection electrodes 14 (also denoted as recording electrodes), which are capable of sensing evoked action potential neural responses to stimulation (eCAPs). Further, appropriate filtering and amplification circuitry (not illustrated) may be provided in the IMD 1 to pass action potentials in the proper band (e.g., for SCS: 500 Hz-2 kHz and 20-200 µV).

Figure 3:
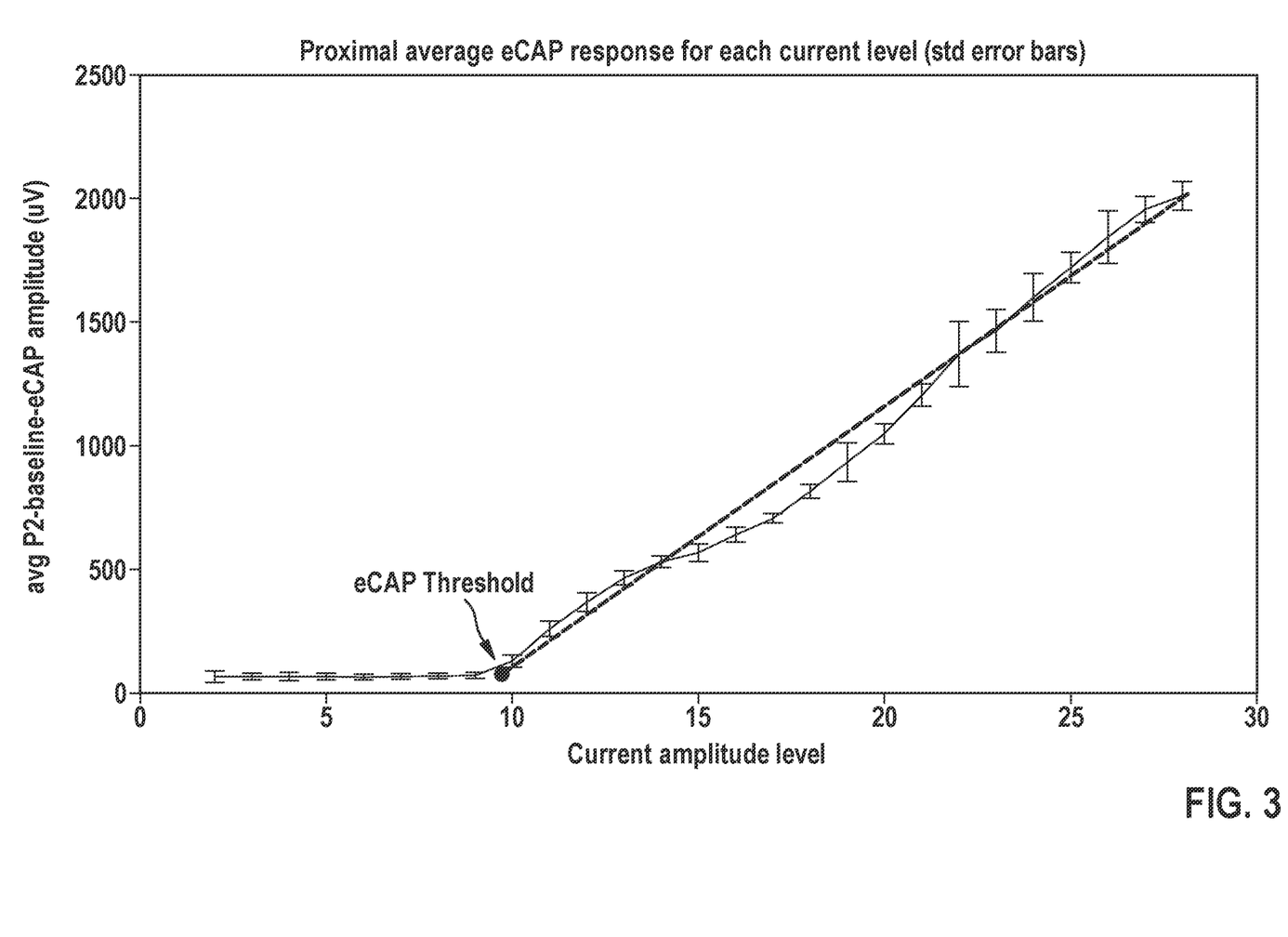
FIG. 3 is a graph exemplarily illustrating an eCAP threshold determination from a linear regression fit to a physiological response.

The IMD 1 is configured for performing an eCAP threshold search by stimulating the neural tissue by means of the electrodes 12 with test stimulation pulses. In particular, during the eCAP threshold search, the IMD 1 may deliver stimulations of a comfortable pulse width, frequency, and initial amplitude. For example, the test stimulation may be delivered via selected therapy electrodes 12 beginning at a low amplitude and with a narrow pulse width (<300 µs) and at a comfortable frequency (40-60 Hz). Then, the stimulation amplitude may be ramped up until eCAPs are sensed by means of the detection electrodes 14. The IMD 1 may then increase the stimulation amplitude by a further 10-20% to ascertain a ratio of a change in eCAP amplitude to a corresponding change in stimulation amplitude (e.g., a stimulation current amplitude). In a diagram depicting the eCAP response as a curve in dependence on the stimulation amplitude as shown in FIG. 3, the ratio may correspond to a slope as measured directly above the eCAP threshold. See FIG. 3 and the corresponding description below for further details of the eCAP search.

The slope and threshold amplitude of eCAP responses may form the basis for the calculation of a coupling factor that is indicative of the stimulation electrodes to the neural tissue. For example, the lower the threshold and greater the slope of eCAP response to amplitude, the greater the coupling of the stimulation system is to the target neural tissue. In another example, lower eCAP thresholds lead to greater coupling factors. One example of use of a coupling factor to translate from one test parameter set with one pulse width to another parameter set for a target therapy with a second pulse width is as follows. An eCAP threshold measurement is performed, with the threshold amplitude determined to be t1 at a pulse width of p1 and a pulse frequency of f1. The coupling factor would be calculated by determining the activation threshold of the target neuronal fiber group as mapped in a strength-duration curve similar to that shown in FIG. 4 at x=p1, and then dividing that amplitude by the eCAP threshold t1. For a target therapy applying a pulse width p2 and frequency f1, the fiber activation threshold could be calculated from the coupling factor by finding the activation threshold of the target neuronal fiber group as mapped in a strength-duration curve similar to that shown in FIG. 4 at x=p2, and dividing this threshold by the coupling factor. For reference in FIG. 4, eCAP signals are typically recorded from axonal fibers at 0.0-0.25 mm depth in the spinal cord, however the same relative strength-duration curve shape applies for all axonal depths.

A similar calculation of the coupling factor may be made to translate between stimulation frequencies using strength-frequency chart as follows. An eCAP threshold measurement is performed, with the threshold amplitude determined to be t1 at a pulse width of p1 and a pulse frequency of f1. The coupling factor would be calculated by determining the activation threshold of the target neuronal fiber group as mapped in a single pulse-width specific strength-frequency curve at x=f1, and then dividing that threshold by the eCAP threshold t1. For a target therapy applying a pulse width p1 and frequency f2, the fiber activation threshold could be calculated from the coupling factor by finding the activation threshold of the target neuronal fiber group as mapped in a strength-frequency curve at x=f2, and dividing this threshold by the coupling factor.

A similar calculation of the coupling factor may be made to translate between stimulation frequencies and pulse widths using a strength-duration-frequency chart as follows. An eCAP threshold measurement is performed, with the threshold amplitude determined to be t1 at a pulse width of p1 and a pulse frequency of f1. The coupling factor would be calculated by determining the activation threshold of the target neuronal fiber group z1 as mapped in a strength-duration-frequency curve at x=f1 and y=p1, and then dividing that threshold by the eCAP threshold t1. For a target therapy applying a pulse width p2 and frequency f2, the fiber activation threshold could be calculated from the coupling factor by finding the activation threshold z2 of the target neuronal fiber group as mapped in a strength-duration-frequency curve at x=f2 and y=p2, and dividing this threshold by the coupling factor.

Likewise, the coupling factor may be used to determine a target starting pulse width in cases where a desired stimulation amplitude already exists. In this way, the coupling factor is also made to translate between stimulation frequencies and pulse widths using a strength-duration-frequency chart as follows. An eCAP threshold measurement is performed, with the threshold amplitude determined to be t1 at a pulse width of p1 and a pulse frequency of f1. The coupling factor would be calculated by determining the activation threshold of the target neuronal fiber group z1 as mapped in a strength-duration-frequency curve at x=f1 and y=p1, and then dividing that threshold by the eCAP threshold t1. For a target therapy applying an amplitude a2 and frequency f2, the fiber activation threshold pulse width could be calculated from the coupling factor by dividing the target stimulation amplitude by the coupling factor and locating this value for the threshold z2 of the target neuronal fiber group as mapped in a strength-duration-frequency curve at x=f2 and then identifying the corresponding threshold pulse width y=p2 representing the threshold pulse width of the target neuronal population at the given stimulation frequency, amplitude, and coupling factor.

In these examples, the chart data and/or calculations may be stored and performed in the programmer, in the implant, or in the patient remote local to the implant.

The IMD 1 is further configured for transmitting a result of the eCAP search to the programmer device 2 via the remote data connection R. To this end, the IMD 1 possesses a transceiver 13.

Likewise, the programmer device 2 comprises a transceiver 23 for entertaining the remote data connection R with the IMD 1. The programmer device 2 is further configured for supporting a generation of a first set of stimulation parameters in dependence on the result of the eCAP threshold search and for transmitting the first set of stimulation parameters to the IMD 1 via the remote data connection R.

The results of the eCAP search may comprise the eCAP threshold amplitude and the coupling factor that is indicative of a coupling between the at least one electrode 12 and the neural tissue. Additionally or alternatively, the programmer device 2 may be configured for determining, based on the results of the eCAP search, the eCAP threshold amplitude and the coupling factor.

Further, the programmer device 2 may be configured for supporting the generation of a first set of stimulation parameters in dependence on the eCAP threshold amplitude and the coupling factor.

The generation of the first set of stimulation parameters may optionally involve a user input (e.g. by a clinician) at the programmer device 2. For example, the user input may be provided by means of a user interface 24 of the programmer device 2. Alternatively, the generation of the first set of stimulation parameters may be effected entirely automatically by the programmer device 2.

Both the IMD 1 and the programmer device 2 comprise a processor 10, 20 and a memory 11, 21 wherein the respective memory 11, 21 has stored a respective computer program that causes the respective processor 10, 20 to execute some or all of the steps in connection with a programming of the IMD 1 as described above or in the following. This is to say that the respective processor 10, 20 (i.e., the processor 10 of IMD 1 or the processor 20 of the programmer device 2) may execute respective method steps that may be carried out by the IMD 1 or the programmer device 2, respectively.

In particular, the processor 10 of the IMD 1 may thus be configured for controlling at least one of the transceiver 13, the electrode(s) 12, and the detector electrodes 14. Correspondingly, the processor 20 of the programmer device 2 may be configured for controlling at least one of the transceiver 23 and the user interface 24.

Figure 2:
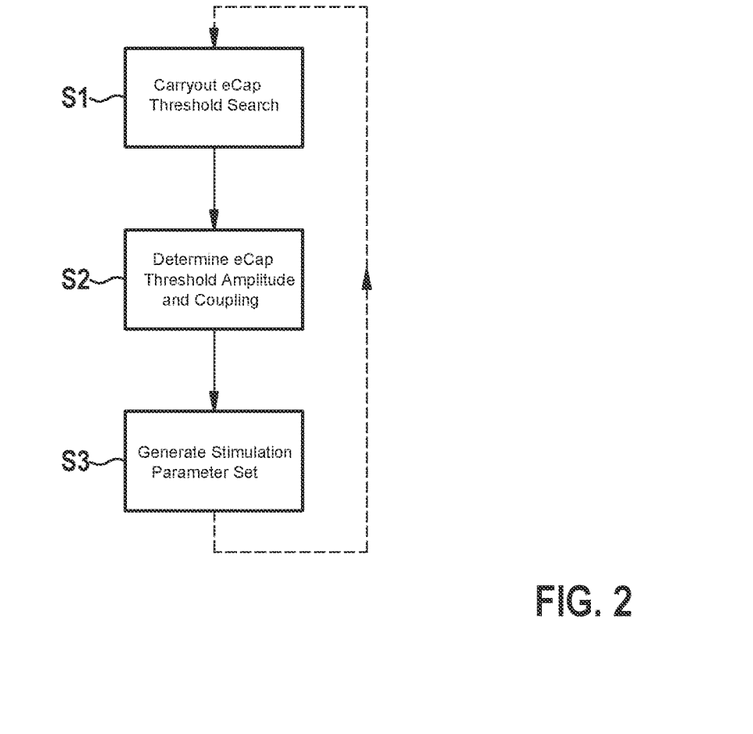
FIG. 2 is a flow chart showing a method according to the instant invention.

FIG. 2 is a schematic and exemplary representation of a general method for programming an IMD 1 that is configured for stimulating neural tissue by means of at least one electrode 12. In a first step S1, an eCAP threshold search is carried out by means of the IMD 1 by stimulating the neural tissue with test stimulation pulses. In a second step S2, each of an eCAP threshold amplitude and a coupling factor are determined based on the eCAP threshold search, wherein the coupling factor is indicative of a coupling between the at least one electrode 12 and the neural tissue. In a third step S3, a first set of stimulation parameters comprising is generated, wherein the first set of stimulation parameters comprises at least a stimulation amplitude that is calculated in dependence on the eCAP threshold amplitude and the coupling factor. For further details regarding the coupling factor, it is referred to the description of FIG. 1 above and FIG. 3 below.

For example, the method may be carried out iteratively, as indicated by the dashed line in FIG. 2. In that case, in one iteration step, the eCAP threshold step is performed in dependence on the first set of stimulation parameters as generated in a preceding iteration step. As a result, the accuracy of the parameter adjustment may be improved.

As a further step (not illustrated in FIG. 2), the method may comprise stimulating, by means of the IMD 1, the neural tissue according to the determined first set of stimulation parameters. The knowledge of the coupling factor may thus be leveraged, such that optimal therapy levels for the patient may be applied. For example, in the context of SCS, therapeutic spinal cord stimulation parameters may thus be adjusted.

For example, the method of FIG. 2 may be carried out as a part of a remote programming scheme using a remote programmer device 2, e.g., as described above with regard to the system 3 of FIG. 1.

In that case, the method may further comprise, before the first step S1 of performing the eCAP threshold search: sending, via a remote data connection R, a second set of stimulation parameters from the programmer device 2 to the IMD 1, wherein the eCAP threshold search is then performed (step S1) in dependence on the second set of stimulation parameters.

In a first variant, the method further comprises, before sending the second set of stimulation parameters: selecting, by means of the programmer device 2, a set of intended stimulation parameters; and determining, by means of the programmer device 2 and in dependence on the set of intended stimulation parameters, the second set of stimulation parameters as a set of test stimulation parameters suitable for the eCAP threshold search. In other words, a clinician may, for example, select a set of stimulation parameters that are a priori intended for therapy based on a clinical analysis of the patient's condition. This set of intended parameters may then be translated into a set of test stimulation parameters that are suitable for the eCAP threshold search before being sent to the IMD 1 as the second set of stimulation parameters.

In a second variant, which is alternative to the first variant, the method comprises, before performing the eCAP threshold search: determining, by means of the IMD 1 and in dependence on the second set of stimulation parameters, a set of test stimulation parameters suitable for the eCAP threshold search, wherein the eCAP threshold search is performed (step S1) in dependence on the set of test stimulation parameters. In this variant, the second set of stimulation parameters may, for example, correspond to a set of intended stimulation parameters selected by a clinician. In contrast to the first variant, a translation into a set of test stimulation parameters suitable for the eCAP threshold search may be carried out by the IMD 1 instead of by the remote programmer device 2.

Figure 4:
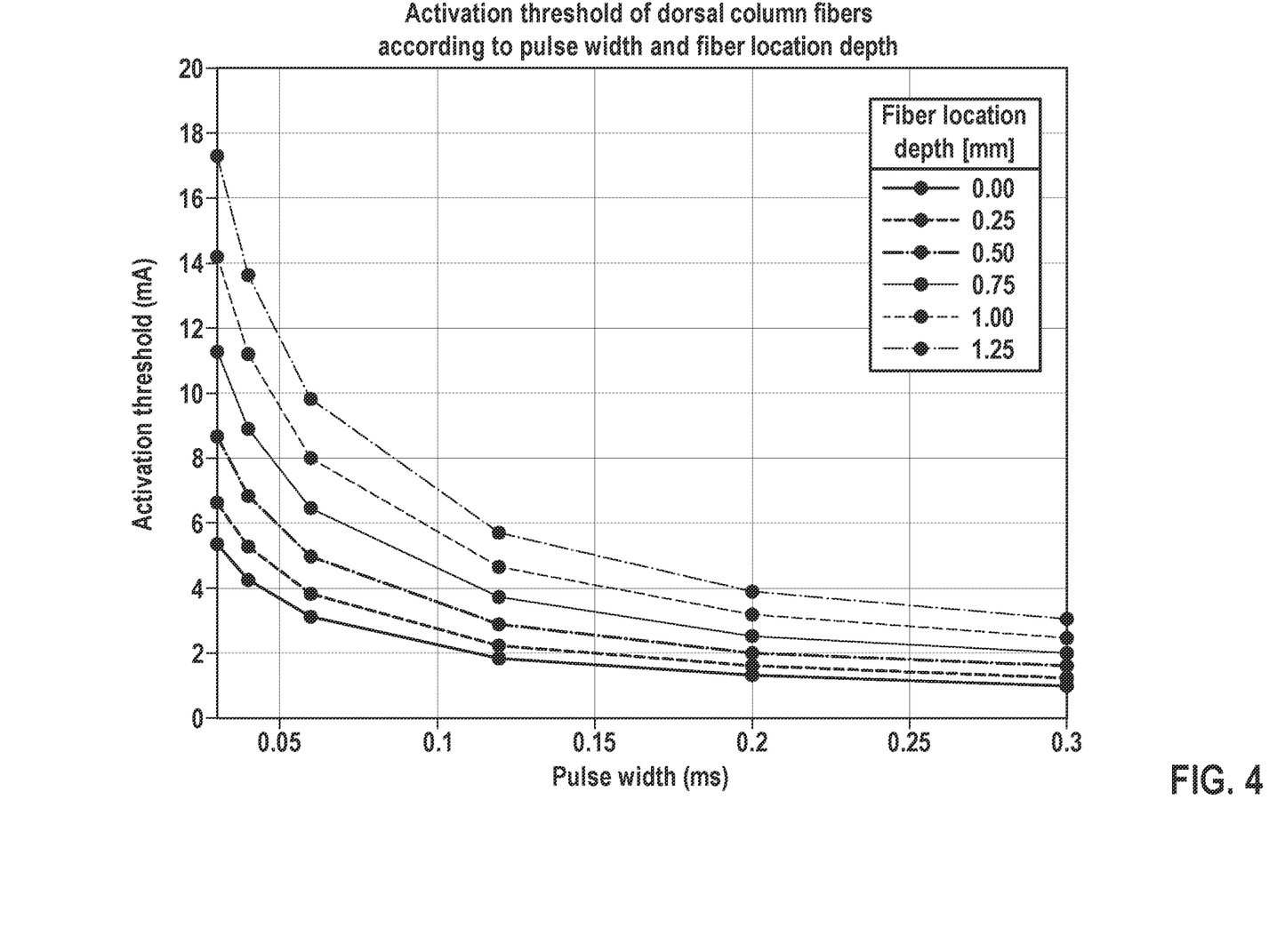
FIG. 4 is a graph showing exemplary strength-duration curves for translating a coupling factor corresponding to a test pulse width into a coupling factor corresponding to a new pulse width.

In accordance with both the first and the second variants described above, the set of test stimulation parameters may be determined, for example, by translating a stimulation pulse width and/or a stimulation frequency of a set of intended stimulation parameters (e.g., in the second variant in the form of the second set of stimulation parameters) into another stimulation pulse width and/or stimulation frequency. For example, the translation may be based on one or more a strength-duration curves and/or on one or more strength-frequency curves that may be stored in a memory 11 of the IMD 1 and/or in a memory 21 of the programmer device 2. Illustrative example of such strength-duration curves are depicted in FIG. 4.

The method may further comprise: sending, via the remote data connection R, a result of the eCAP threshold search from the IMD 1 to the programmer device 2; generating (step S3), by means of the programmer device 2, the first set of stimulation parameters based on the result; and sending, via the remote data connection R, the first set of stimulation parameters from the programmer device 2 to the IMD 1. The generation of the first set of stimulation parameters may optionally involve a user input (e.g. by a clinician) via a user interface 24 of the programmer device 2. Alternatively, the generation of the first set of stimulation parameters may be effected entirely automatically by the programmer device 2.

In the following, a further embodiment of a remote programming scheme in connection with SCS will be described: As a preparatory step, prior to a stimulation adjustment, the clinician may establish that the placement of the leads adjacent to the spinal cord of the patient allows for a recording of eCAPs at comfortable levels of stimulation. As described above, for a remote programming session, the patient's IMD 1 must be in communication with a remote programmer device 2. In other words, a device system 3 comprising the IMD 1 and the programmer device 2, as exemplarily depicted in FIG. 1, is required. When a new electrode configuration or other stimulating parameter set is desired to be sent to the IMD 1 for patient use, comfortable operating parameter ranges which minimize side effect must be established. After the clinical user of the remote programming control unit has defined a target parameter set (i.e., a set of intended stimulation parameters), the system 3 (either within the remote programmer device 2 or within the IMD 1 itself) adapts the parameters to appropriate values to perform an eCAP search (i.e., a set of test stimulation parameters). For example, the frequency and pulse width are adapted for patient comfort during the stimulation. The IMD 1 is then commanded to execute the eCAP search function (step S1) with those parameters and electrodes 12 (i.e., based on a set of test stimulation parameters). The eCAP search function maintains the electrodes 14, pulse width, and frequency of the test parameter set and systematically increases the amplitude while sensing evoked responses by means of the detection electrodes 14 with each step in amplitude. The system 3 stores the magnitude of the sensed evoked responses for analysis. This eCAP search function is executed quickly and automatically and does not require patient input during operation. The sensed evoked responses are used to compute (step S2) the electrode/tissue coupling factor, which is based on a combination of the eCAP threshold and the stimulation parameters used to evoke the eCAP response as previously described. The electrode/tissue coupling factor may be calculated from the eCAP search results transmitted to the programmer device 2 by means of the programmer device 2 (optionally with manual input from the user).

Alternatively, the calculation of the coupling factor may be incorporated within an algorithm in the IMD 1 itself. Then, the coupling factor is used (step S3) for the selection of a final amplitude range (i.e., the first set of stimulation parameters) of the desired program that uses the tested electrodes 12.

If a pulse width of the comfortable test stimulation is not the same as the desired final program pulse width, an amplitude translation based on a strength-duration curve (cf. FIG. 4) may be applied to translate the coupling factor into a scale relevant to the therapeutic pulse width. A similar translation may be applied for differences in frequency between the eCAP threshold search frequency and the target therapeutic frequency.

For programs which use the same pulse width and other parameters as the eCAP threshold search, a basic calculation establishing a comfortable operating range may then be applied. Based on tests, on average a comfortable operating range for SCS stimulation reaches up to the eCAP threshold stimulation amplitude plus 20%. This range may be programmed into the IMD 1 as a usable range for therapy of the patient (i.e., as the first set of parameters or a part thereof).

For therapies other than SCS and for other neural targets, the target therapy amplitude relative to eCAP amplitude must be intrinsically determined for any given therapy and neural target. Once this is determined, it can be applied to field remote programming operations when the patient-specific coupling factor has been determined by the eCAP search.

FIG. 3 schematically and exemplarily illustrates an eCAP threshold determination from a linear regression fit to a physiological response. The IMD 1 carries out an eCAP threshold search by increasing the stimulation amplitude in incremental steps until an eCAP is recorded at at least 2 consecutive amplitudes, preferably at least 4 amplitudes within 10-15% of the initial eCAP detection amplitude. The measured response data may be processed within a linear fit model to establish a precise neural activation threshold. For example, the precise eCAP threshold may be determined as an intersection of two linear regression curves, namely a linear fit to a section of the curve above the onset of the eCAPs and a linear fit to a (essentially horizontal) section of the curve below the onset of the eCAPs. This eCAP threshold may be used to establish the electrode-spinal cord electrical coupling factor for therapy determination in the following steps.

FIG. 4 shows exemplary strength-duration curves for translating a coupling factor corresponding to a test pulse width into a coupling factor corresponding to a new pulse width. Different curves correspond to different electrode-to-neuron distances. In order to translate the lead coupling factor from a test pulse width into a coupling factor corresponding to a new pulse width which will be used by a therapy program, the known strength-duration curve function for the target neuron type should be applied. The ratio of the activation thresholds on the strength-duration curve of the two different pulse widths can be multiplied by the frequency-determined coupling factor to obtain the new stimulation threshold for the new pulse width. Preferably, the coupling factor would be calculated as previously described taking into account pulse width and frequency of the test stimulation. For sub-perception stimulation, the therapy amplitude may be calculated by multiplying the translated coupling factor by a value less than 1, typically in the range of 0.1-0.6. For paresthesia-based therapy, the therapy amplitude may be calculated by multiplying the translated coupling factor by a value of typically 1.0-1.15.

Figure 5:
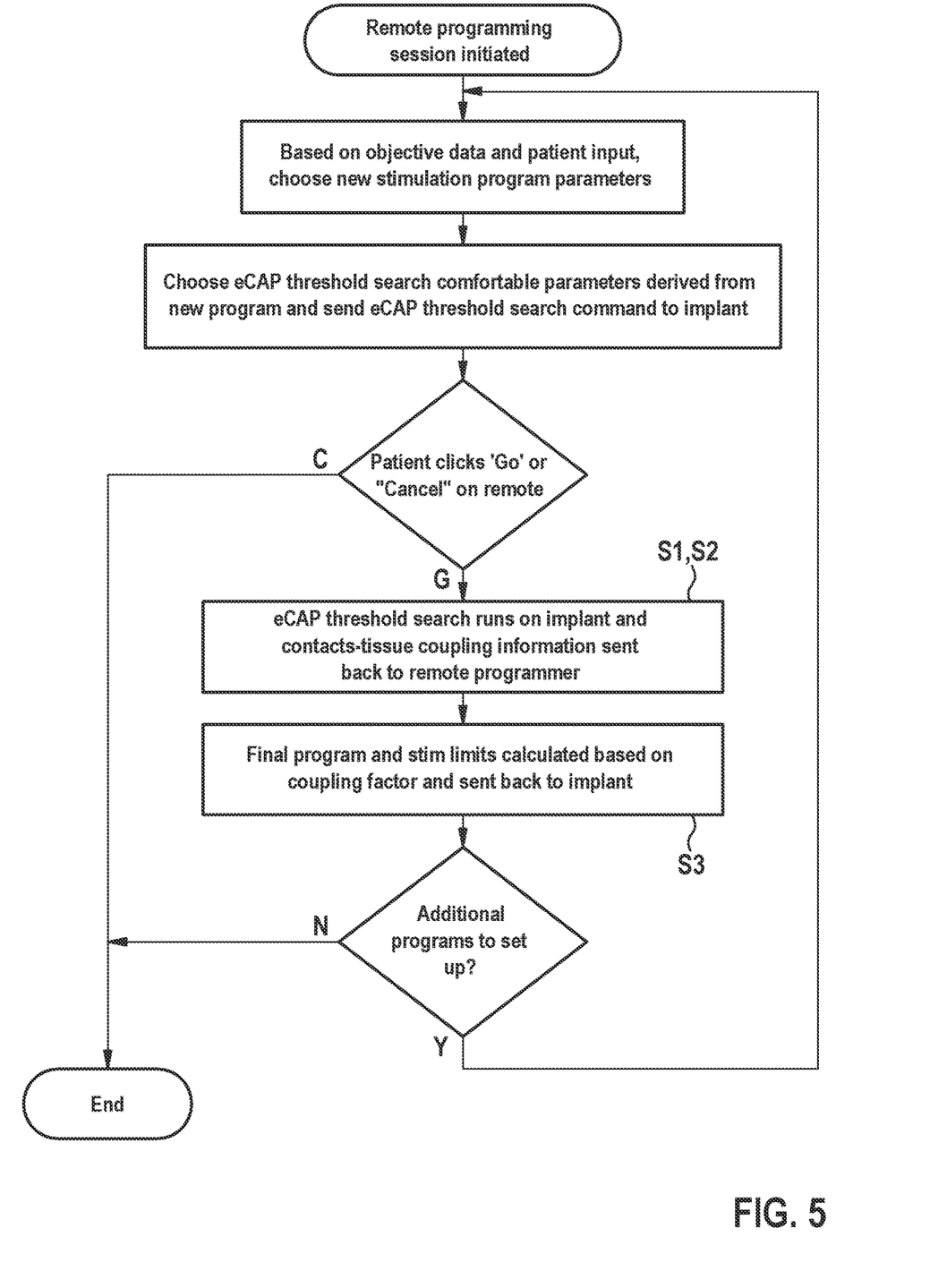
FIG. 5 is a flow chart illustrating an exemplary embodiment of a method of remotely programming an implantable medical device.

FIG. 5 schematically and exemplarily illustrates an exemplary embodiment of a method of remote programming an implantable medical device in the form of a flow diagram. According to this exemplary embodiment, after initiation of a remote programming session, new stimulation program parameters (i.e., a set of intended stimulation parameters) are chosen based on objective data and/or patient input. Then, comfortable parameters for an eCAP threshold search (i.e., a set of suitable test stimulation parameters) are derived from the new program parameters. Subsequently, the patient decides whether the programming session shall end or continue by selecting "Cancel" or "Go", respectively, on the patient remote 22. In case the patient has selected to continue the programming session, an eCAP threshold search is carried out by the IMD 1 (step S1), and information regarding the electrode-tissue coupling are determined (step S2) and sent back to the remote programmer device 2. The programmer device 2 then calculates (step S3) a final program (for therapy), including stimulation limits (i.e., the first set of stimulation parameters) and sends those back to the IMD 1. Finally, if there are no additional programs to set up, the programming session end. Otherwise, the session starts again with the step of choosing new stimulation program parameters.

Figure 6:
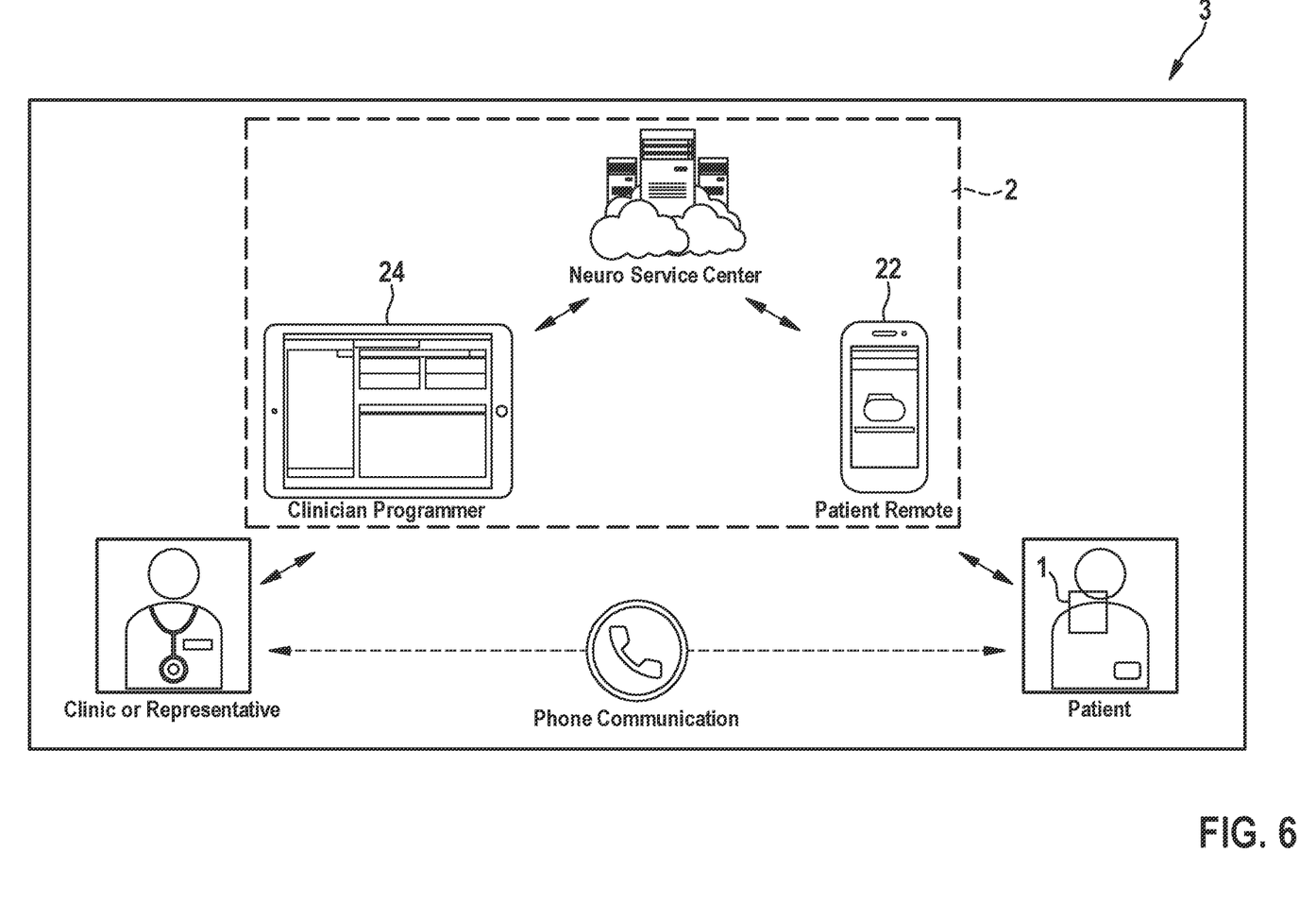
FIG. 6 is an illustration showing data flow during a remote programming process in accordance with one or more embodiments.

FIG. 6 schematically and exemplarily illustrates a data flow during a remote programming process in accordance with one or more embodiments. FIG. 7 schematically and exemplarily illustrates a display content of a patient remote during the remote programming process illustrated in FIG. 6. In the following, reference will be made to both FIGS. 6 and 7.

As illustrated in FIG. 6, in the present embodiment, the programmer device 2 is or comprises a clinician's programmer. The clinician's programmer 2 communicates with a Neuro Service Center, which, in turn, communicates with a patient remote 22 carried by the patient. In the present embodiment, the ensemble of the clinician's programmer, the Neuro Service Center, and the patient remote 22 may also be considered as a programmer device 2 as they work together to form the programming communication channel to the device.

Initially, the clinician or designated representative establishes a phone communication connection with the patient. The clinician uses the clinician's programmer 2 to locate the patient-specific data within the Neuro Service Center. Once the clinician has selected the desired patient, the Neuro Service Center is used to establish a connection from the clinician's programmer 2 to the patient remote 22 and (optionally) the implantable medical device 1. The clinician may query monitoring data in order to objectively assess pain indicators and program usage data. Additionally, the clinician may have a discussion with the patient regarding his or her pain experience and resulting adjustment needs. Based on this information, the clinician may define a program change or a new program (i.e., a set of intended stimulation parameters) via the user interface 24 of the clinician programmer 2. Once the set of intended stimulation parameters is selected, it is transmitted from the clinician's programmer to the implantable medical device 1 via the Neuro Service Center and (optionally) the patient remote 22.

Figure 7A:
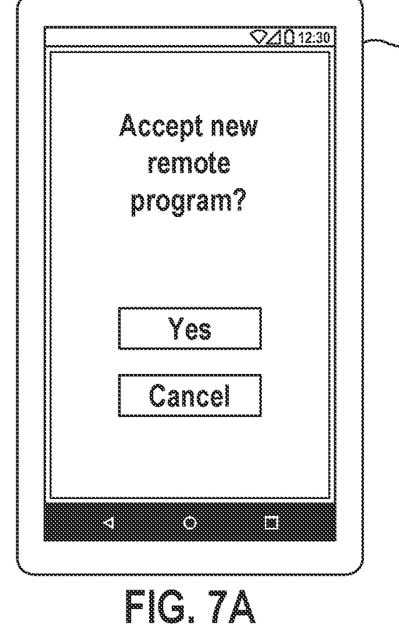
FIGS. 7A-7D are illustrations showing a display content of a patient remote during a remote programming process.
Figure 7B:
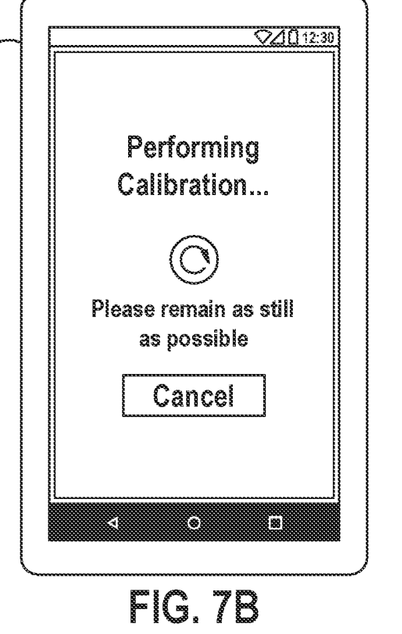
Figure 7C:
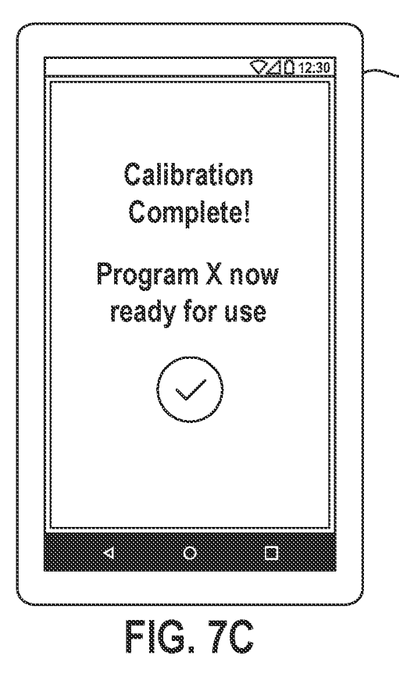
Figure 7D:
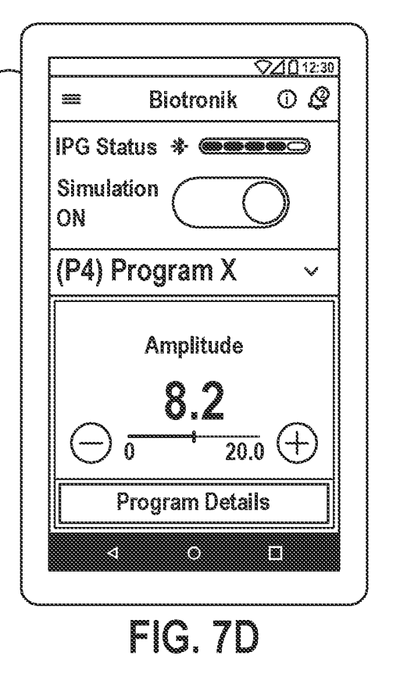

Following the transmission of the new program (i.e., the set of intended stimulation parameters), in this embodiment of the invention, the patient sees a message on the display of the patient remote 22 that requires acceptance of the new program (FIG. 7A). After the patient accepts receipt of the new program, the patient sees a message indicating that a calibration is occurring (FIG. 7B). The message may further instruct the patient to remain still. Additionally or alternatively, the clinician can provide directions to the patient via phone. During this time, the eCAP search algorithm is running on the IMD 1, as described above. As further described above, one or more stimulation amplitudes for the new program may be automatically defined based on an eCAP-based algorithm. Once the search algorithm is complete and specific stimulation amplitudes have been calculated, the patient remote 22 informs the patient that the new program (based on the first set of stimulation parameters) is ready for use (see FIG. 7C). Once the patient acknowledges this message, the patient is able to navigate to the new program via the patient remote (see FIG. 7D).

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

LIST OF REFERENCE SIGNS

1 Implantable medical device
10 Processor
11 Memory
12 Electrode(s)
13 Transceiver
14 Detection electrode(s)
2 Programmer device
20 Processor
21 Memory
22 Patient remote
23 Transceiver
24 User Interface
3 System
R Remote connection
S1, S2, S3 Method steps

The invention claimed is:

1. A method for programming an implantable medical device configured for stimulating neural tissue by means of at least one electrode, the method comprises the steps of:
performing, by means of the implantable medical device, an evoked compound action potential (eCAP) threshold search by stimulating the neural tissue with test stimulation pulses;
determining, based on the eCAP threshold search, an eCAP threshold amplitude and a coupling factor that is indicative of a coupling between the at least one electrode and the neural tissue; and
generating a first set of stimulation parameters having at least a stimulation amplitude that is determined in dependence on the eCAP threshold amplitude and the coupling factor.

2. The method according to claim 1, which further comprises carrying out the method iteratively in such a way that, in an iteration step, an eCAP threshold step is performed in dependence on the first set of stimulation parameters as generated in a preceding iteration step.

3. The method according to claim 1, which further comprises determining the coupling factor in dependence on the eCAP threshold amplitude and stimulation parameters of an eCAP measurement.

4. The method according to claim 3, wherein a lower the eCAP threshold amplitude a higher the coupling factor, and wherein a shorter duration of a stimulating pulse width a greater the coupling factor.

5. The method according to claim 1, further comprising stimulating, by means of the implantable medical device, the neural tissue according to the first set of stimulation parameters.

6. The method according to claim 1, which further comprises forming the test stimulation pulses to be shorter than 300 µs.

7. The method according to claim 1, which further comprises delivering the test stimulation pulses with a stimulation frequency in a range from 40 Hz to 60 Hz.

8. The method according to claim 1, wherein the eCAP threshold search includes delivering stimulation with consecutive test stimulation pulses having an increasing amplitude until an eCAP is detected for at least two consecutive amplitudes.

9. The method according to claim 1, which further comprises, before initiating the performing step:
sending, via a remote data connection, a second set of stimulation parameters from a programmer device to the implantable medical device, and wherein the eCAP threshold search is performed in dependence on the second set of stimulation parameters.

10. The method according to claim 9, which further comprises, before sending the second set of stimulation parameters, performing the further steps of:
selecting, by means of the programmer device, a set of intended stimulation parameters; and
determining, by means of the programmer device and in dependence on the set of intended stimulation parameters, the second set of stimulation parameters as a set of test stimulation parameters suitable for the eCAP threshold search.

11. The method according to claim 10, which further comprises determining the set of test stimulation parameters by translating a stimulation pulse width and/or a stimulation frequency of the set of intended stimulation parameters into another stimulation pulse width and/or stimulation frequency.

12. The method according to claim 9, which further comprises, before initiating the performing step:
determining, by means of the implanted medical device and in dependence on the second set of stimulation parameters, a set of test stimulation parameters suitable for the eCAP threshold search, wherein the eCAP threshold search is performed in dependence on the set of test stimulation parameters.

13. The method according to claim 9, which further comprises:
sending, via the remote data connection, a result of the eCAP threshold search from the implantable medical device to the programmer device;
generating, by means of the programmer device, the first set of stimulation parameters based on the result; and
sending, via the remote data connection, the first set of stimulation parameters from the programmer device to the implantable medical device.

14. The method according to claim 1, wherein the eCAP threshold amplitude represents an amplitude below which there is no detectable eCAP.

15. A system for configuring stimulation parameters, the system comprising:
an implantable medical device having at least one electrode and configured for stimulating neural tissue by means of said at least one electrode; and
a programmer device having a remote data connection with said implantable medical device, said implantable medical device being configured for performing an evoked compound action potential (eCAP) threshold search by stimulating the neural tissue with test stimulation pulses and for transmitting a result of the eCAP threshold search to said programmer device via said remote data connection;
said programmer device being configured for supporting a generation of a first set of stimulation parameters in dependence on the result of the eCAP threshold search and for transmitting the first set of stimulation parameters to said implantable medical device via said remote data connection, wherein:

the results of the eCAP threshold search have an eCAP threshold amplitude and a coupling factor that is indicative of a coupling between said at least one electrode and the neural tissue; and/or said programmer device is configured for determining, based on the results of the eCAP threshold search, the eCAP threshold amplitude and the coupling factor that is indicative of the coupling between said at least one electrode and the neural tissue.

16. The system according to claim 15, wherein said implantable medical device and/or said programmer device has a processor and a memory, said memory has stored therein a computer program that causes said processor to execute method steps for programming said implantable medical device, said processor programmed to:

perform, by means of said implantable medical device, the evoked compound action potential (eCAP) threshold search by stimulating the neural tissue with the test stimulation pulses;

determine, based on the eCAP threshold search, the eCAP threshold amplitude and the coupling factor that is indicative of the coupling between said at least one electrode and the neural tissue; and generate the first set of stimulation parameters having at least the stimulation amplitude that is determined in dependence on the eCAP threshold amplitude and the coupling factor.

17. The system according to claim 15, wherein the eCAP threshold amplitude represents an amplitude below which there is no detectable eCAP.

\* \* \* \* \*